US009410167B2

(12) United States Patent
Cho et al.

(10) Patent No.: US 9,410,167 B2
(45) Date of Patent: *Aug. 9, 2016

(54) CELLS OR PLANTS PRODUCING POLYLACTATE OR ITS COPOLYMERS AND USES THEREOF

(75) Inventors: Jun-Hyeong Cho, Daejeon (KR); Si-Jae Park, Daejeon (KR); Sang-Yup Lee, Daejeon (KR); Yu-Kyung Jung, Daejeon (KR)

(73) Assignees: LG CHEM, LTD., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 1851 days.

This patent is subject to a terminal disclaimer.

(21) Appl. No.: 11/439,517

(22) Filed: May 24, 2006

(65) Prior Publication Data
US 2007/0277268 A1 Nov. 29, 2007

(30) Foreign Application Priority Data

May 24, 2005 (KR) .................. 10-2005-0043798

(51) Int. Cl.
| C12N 15/70 | (2006.01) |
| C12N 15/74 | (2006.01) |
| C12P 7/62 | (2006.01) |
| C12N 9/10 | (2006.01) |
| C12N 9/00 | (2006.01) |
| C12N 15/82 | (2006.01) |

(52) U.S. Cl.
CPC . C12P 7/625 (2013.01); C12N 9/10 (2013.01); C12N 9/93 (2013.01); C12N 15/70 (2013.01); C12N 15/74 (2013.01); C12N 15/8242 (2013.01); C12N 2500/35 (2013.01); Y02P 20/52 (2015.11)

(58) Field of Classification Search
None
See application file for complete search history.

(56) References Cited

U.S. PATENT DOCUMENTS

| 6,103,956 | A | 8/2000 | Srienc et al. |
| 6,143,952 | A | 11/2000 | Srienc et al. |
| 8,114,643 | B2 * | 2/2012 | Skraly et al. ............. 435/135 |
| 8,383,379 | B2 * | 2/2013 | Park et al. ............. 435/183 |
| 8,765,402 | B2 * | 7/2014 | Park et al. ............. 435/41 |
| 2010/0050298 | A1 * | 2/2010 | Park et al. ............. 800/298 |

FOREIGN PATENT DOCUMENTS

| KR | 10-0250830 | 4/2000 |
| KR | 10-0447531 | 8/2004 |
| WO | WO 94/11519 | 5/1994 |
| WO | WO 98/54329 | 12/1998 |
| WO | WO 99/61624 | 12/1999 |
| WO | WO 01/55436 | 8/2001 |

OTHER PUBLICATIONS

Taguchi et al. PNAS, Nov. 11, 2008; vol. 105, No. 45 pp. 17323-17327.*
Valentin et al. Application of a propionyl coenzyme A synthetase for poly(2-hydroxypropionate-co-3-hydroxybutyrate) accumulation in recombinant *E. coli*. Applied and Environmental Microbiology. 2000. 66(12): 5253-5258.*
Jossek et al. In vitro synthesis of poly(3-hydrobutyric acid) by using an enzymatic coenzyme A recycling system. FEMS Microbiology Letters. 1998. 168: 319-324.*
Valentin et al. Application of enzymatically synthesized short-chain-length hydroxy fatty acid coenzyme A thioesters for assay of polyhydroxyalkanoic acid synthases. Applied Microbiology Biotechnology. 1994. 40: 699-709.*
Steinbuchel et al. (FEMS Microbiology Letters 128; 1995, pp. 219-228).*
Scheper (editor). Biopolyesters. Advances in Biochemical Engineering/Biotechnology. Springer: Berlin. 2001 pp. 60-66 and 72.*
Park et al. Metabolic engineering of *Escherichia* cells for the production of medium-chain-length polyhydroxyalkanoates rich in specific monomers. FEMS Microbiology Letters. 2002. 214: 217-222.*
Yang et al. Tailor-made type II Pseudomonas PHA synthases and their use for the biosynthesis of polylactic acid and its copolymer in recombinant *Eschericia coli*. Appl. Microbiol. Biotechnol. 2011. 90: 603-614.*
Anderson et al. Occurrence, metabolism, metabolic rate, and industrial uses of bacterial polyhydroxyalkanoates. Micriobiological Reviews. 1990. 54(4): 450-472.*
Abe H et al: "Physical Properties and Enzymatic Degradability of Copolymers (R)-3-hydroxybutyric acid and (S, S)-lactide" Polymer, Elsevier Science Publishers B.V., GB, vol. 39, No. 1 (Jan. 1, 1998).
Nawrath C. et al: "Plastid Targeting of the Enzymes Required for the Production of Polyhydroxybutyrate in Higher Plants" Studies in Polymer Science, Elsevier Science Publishers B.V., Amsterdam, NL, vol. 12 (Jan. 1, 1994).
Qi et al., *FEMS Microbiol. Lett.*, 157: pp. 155-162, 1997.
Qi et al., *FEMS Microbiol. Lett.*, 167: pp. 89-94, 1998.
Langenbach et al., *FEMS Microbiol. Lett.*, 150: pp. 303-309, 1997.
Taguchi et al., *FEMS Microbiol. Lett.*, 176: pp. 183-190, 1999.
Ren et al., *J. Bacteriol.*, 182: pp. 2978-2981, 2000.

(Continued)

Primary Examiner — Russell Kallis
Assistant Examiner — Ashley K Buran
(74) Attorney, Agent, or Firm — Dentons US LLP

(57) ABSTRACT

The present invention relates to cells or plants that can produce polylactate or its copolymers and to a method for preparing polylactate or its copolymers using the same. More specifically, cells or plants with the ability to produce polylactate or hydroxyalkanoate-lactate copolymers comprise both a gene encoding an enzyme that converts lactate into lactyl-CoA and a gene encoding polyhydroxyalkanoate (PHA) synthase which uses lactyl-CoA as a substrate. Also described is a method for preparing polylactate or hydroxyalkanoate-lactate copolymers which comprises culturing the cells in a medium containing lactate or lactate and various hydroxyalkanoates or culturing the plants. Effective preparation of hydroxyalkanoate-lactate copolymer which comprises various hydroxyalkanoates as well as polylactate, using the cells or the plants, is disclosed.

6 Claims, 7 Drawing Sheets

(56) References Cited

OTHER PUBLICATIONS

Park et al., *FEMS Microbiol. Lett.*, 214: pp. 217-222, 2002.
Zhang et al., *Appl. Microbiol. Biotechnol.*, 56: pp. 131-136, 2001.
Valentin and Steinbuchel, *Appl. Microbiol. Biotechnol.*, 40: pp. 699-709, 1994.
Yuan et al., *Arch. Biochem. Biophyics.*, 394: pp. 87-98, 2001.
Lee, *Biotechnol. Bioeng.*, 49: pp. 1-14, 1996.
Steinbüchel and Valentin, *FEMS Microbiol. Lett.*, 128: pp. 219-228, 1995.
Selmer et al., *Eur J. Biochem.*, 269: pp. 372-380, 2002.
Park and Lee, *J. Bacteriol.*, 185: pp. 5391-5397, 2003.
Kovach et al., *Gene*, 166: pp. 175-176, 1995.
Jung et al., Biotechnology and Bioengineering, vol. 105, No. 1, pp. 161-171, Jan. 1, 2010.
Yang et al., Biotechnology and Bioengineering, vol. 105, No. 1, pp. 150-160, Jan. 1, 2010.
Moire et al., J. Plant Physiol, 160. pp. 831-839, 2003.
Bongcam, V. et al., Biofutur, Lavoisier, Cachan, FR vol. 1998, No. 184, (Dec. 1, 1998), pp. 84-85.
Park et al., Applied Biochemistry and Biotechnology, vol. 113-116, pp. 335-346, 2004.
Takagi et al., Journal of Bioscience and Bioengineering, vol. 98, No. 6, pp. 477-481, 2004.

\* cited by examiner

```
                       SEQUENCE LISTING

<160> NUMBER OF SEQ ID NOS: 4

<210> SEQ ID NO 1
   <211> LENGTH: 39
   <212> TYPE: DNA
   <213> ORGANISM: Artificial sequence
   <220> FEATURE:
   <223> OTHER INFORMATION: primer

<400> SEQUENCE: 1
ggaattcatg agaaaggttc ccattattac cgcagatga                              39

<210> SEQ ID NO 2
   <211> LENGTH: 46
   <212> TYPE: DNA
   <213> ORGANISM: Artificial sequence
   <220> FEATURE:
   <223> OTHER INFORMATION: primer

<400> SEQUENCE: 2
gctctagatt aggacttcat ttccttcaga cccattaagc cttctg                      46

<210> SEQ ID NO 3
   <211> LENGTH: 27
   <212> TYPE: DNA
   <213> ORGANISM: Artificial sequence
   <220> FEATURE:
   <223> OTHER INFORMATION: primer

<400> SEQUENCE: 3
ggaattcatg aattgtttca aaaacga                                           27

<210> SEQ ID NO 4
   <211> LENGTH: 28
   <212> TYPE: DNA
   <213> ORGANISM: Artificial sequence
   <220> FEATURE:
   <223> OTHER INFORMATION: primer

<400> SEQUENCE: 4
cgggatcctt aattagaacg ctcttcaa                                          28
```

CELLS OR PLANTS PRODUCING POLYLACTATE OR ITS COPOLYMERS AND USES THEREOF

BACKGROUND OF THE INVENTION

1. Field of the Invention

The present invention relates to cells or plants having the ability of producing polylactate or its copolymers and a method for preparing polylactate or its copolymers using the same, more specifically, relates to cells or plants capable of expressing a gene encoding an enzyme converting lactate into lactyl-CoA and a gene encoding an enzyme involved in PHA synthesis and a method for preparing polylactate or hydroxyalkanoate-lactate copolymer, the method comprises: culturing the cells in a medium containing lactate, carbon sources providing hydroxyalkanoyl-CoA or lactate and various hydroxyalkanoate, or culturing the plants.

2. Description of the Background Art

Polylactate (PLA) is a typical biodegradable polymer originated from lactate, which has a variety of applications as a common or a medical polymer. At present, PLA is being prepared by polymerizing lactate which is produced by fermenting microorganisms, but only low molecular weight PLA (1000-5000 dalton) is produced by direct polymerization of lactate. To synthesize high molecular weight (>100,000 dalton) of PLA, a method polymerizing low molecular weight PLA obtained by direct polymerization of lactate using a chain coupling agent to obtain higher molecular weight PLA can be used. But it has disadvantages in that, the process for preparing PLA of high molecular weight is complicated due to the addition of a solvent or a chain coupling agent and also it isn't easy to remove them. At present, in the process for preparing commercially available PLA of high molecular weight, a method, in which lactate is converted into lactide to synthesize PLA by cyclodehydration of the lactide ring, is being used.

Meanwhile, PHA is a polyester which microorganisms accumulate therein as a carbon and energy storage compound when other nutritive elements, for example, phosphorus, nitrogen, magnesium, oxygen, are deficient while the carbon source is in excess. PHA is recognized as an alternative material for existing synthesized plastics since it has similar properties to synthetic polymers originating from petroleum, and, at the same time, shows an excellent biodegradation rate.

The existing PHA is divided into SCL-PHA(short-chain-length PHA) having short carbon chains and MCL-PHA(medium-chain-length PHA) having long carbon chains. A gene synthesizing PHA was cloned from *Ralstonia eutropha*, *Pseudomonas* and, PHA consisting of various monomers was synthesized by recombinant microorganisms (Qi et al., *FEMS Microbiol. Lett.*, 157:155, 1997; Qi et al., *FEMS Microbiol. Lett.*, 167:89, 1998; Langenbach et al., *FEMS Microbiol. Lett.*, 150:303, 1997; WO 01/55436; U.S. Pat. No. 6,143,952; WO 98/54329; WO 99/61624).

To produce PHA in microorganisms, an enzyme which converts metabolites into a PHA monomer and PHA synthase which synthesizes the PHA polymer using the PHA monomers are required. PHA synthase synthesizes PHA using hydroxyacyl-CoA as a substrate and β-ketothiolase (PhaA), acetoacetyl-CoA reductase (PhaB), cloned from *Ralstonia eutropha* etc., 3-hydroxydecanoyl-ACP:CoA transferase (PhaG) cloned from *Pseudomonas*, (R)-specific enoyl-CoA hydratase (PhaJ) derived from *Aeromonas caviae* and *Pseudomonas aeruginosa* (Fukui et al., *J. Bacteriol.*, 180: 667, 1998; Tsage et al., *FEMS Microbiol. Lett.*, 184:193, 2000), 3-ketoacyl-ACP reductase (FabG) derived from *E. coli* and *Pseudomonas aeruginosa* (Taguchi et al., *FEMS Microbiol. Lett.*, 176:183, 1999; Ren et al., *J. Bacteriol.*, 182:2978, 2000; Park et al., *FEMS Microbiol. Lett.*, 214:217, 2002) are known as enzymes capable of generating hydroxyacyl-CoA which is a substrate of PHA. Various kinds of PHAs have been synthesized with these enzymes using hydroxyalkanoates hydroxylated at various positions in the carbon chain (mainly the 3, 4, 5, and 6 positions). However, it has been reported that it has little PHA synthase activity on hydroxyalkanoate which is hydroxylated at the 2-position (Zhang et al., *Appl. Microbiol. Biotechnol.*, 56:131, 2001; Valentin and Steinbuchel, *Appl. Microbiol. Biotechnol.*, 40:699, 1994; Yuan et al., *Arch. Biochem. Biophyics.*, 394:87, 2001). Thus far, there have been reports of PHA synthase activity on lactyl-CoA measured in vitro as PHA polymerase activity on lactyl-CoA. However, but PHA synthase activity on lactyl-CoA is very weak (Zhang et al., *Appl. Microbiol. Biotechnol.*, 56:131, 2001; Valentin and Steinbuchel, *Appl. Microbiol. Biotechnol.*, 40:699, 1994). That is, there are no examples of natural production or production by recombinant cells of PHA and its copolymers because a hydroalkanoate, such as lactate hydroxylated at the 2-carbon position, is not a suitable substrate for PHA synthase.

Therefore, the present inventors have expended extensive efforts to produce high molecular weight PLA and its copolymers using cells or plants. As disclosed herein, they have discovered that that poly[hydroxyalkanoate-co-lactate] copolymers is produced by culturing recombinant *Ralstonia eutropha* transformed with the propionyl-CoA transferase gene (pct) derived from *Clostridium propionicum* which is a gene encoding an enzyme that converts lactate into lactyl-CoA in a production medium containing lactate. PLA was produced by culturing in a production medium containing lactate the recombinant *E. coli* transformed with the PHA synthase gene derived from *Bacillus cereus* and the pct gene.

SUMMARY OF THE INVENTION

An objective of the present invention is to provide cells or plants that have the ability to produce PLA or its copolymers [poly(hydroxyalkanoate-co-lactate)].

Another objective is to provide a method for preparing polylactate or its copolymers by culturing these cells or plants.

To achieve the above objectives, in one aspect, the present invention provides a cell or plant having the ability to produced polylactate or hydroxyalkanoate-lactate copolymers [poly(hydroxyalkanoate-co-lactate)], which cell or plant has both a gene encoding an enzyme which converts lactate to lactyl-CoA and a gene encoding polyhydroxyalkanoates (PHA) synthase which can use lactyl-CoA as a substrate.

In another aspect, the present invention provides a method for preparing polylactate or hydroxyalkanoate-lactate copolymers[poly(hydroxyalkanoate-co-lactate)], comprising (a) culturing the cells in a medium containing lactate or lactate and hydroxyalkanoate as a carbon source and recovering polylactate or hydroxyalkanoate-lactate copolymers [poly(hydroxyalkanoate-co-lactate)] from the cultured cells or (b) culturing the plants and recovering polylactate or hydroxyalkanoate-lactate copolymer from the cultured plants.

In still another aspect, the present invention provides a recombinant vector for preparing polylactate or hydroxyalkanoate-lactate copolymers[poly(hydroxyalkanoate-co-lactate)] which vector comprises contains a gene encoding an enzyme that converts lactate into lactyl-CoA and a gene encoding PHA synthase that uses lactyl-CoA as a substrate. Also provided is a cell or a plant transformed with the above recombinant vector.

In yet another aspect, the present invention provides a method for preparing polylactate or hydroxyalkanoate-lactate copolymers[poly(hydroxyalkanoate-co-lactate)], comprising the steps of (a) culturing the transformed cells in a medium containing lactate or hydroxyalkanoate and as a carbon source; and recovering polylactate or hydroxyalkanoate-lactate copolymers from the cultured cells or (b) culturing transformed plants and recovering polylactate or hydroxyalkanoate-lactate copolymer from the cultured plants.

In yet another aspect, the present invention provides hydroxyalkanoate-lactate copolymers[poly(hydroxyalkanoate-co-lactate)], containing, as a monomer, lactate and one or more hydroxyalkanoates selected from the group consisting of 3-hydroxybutyrate, 3-hydroxyvalerate, 4-hydroxybutyrate, (D)-3-hydroxycarboxylic acids of the medium chain length (C6-14), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methyhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyl-decanoic acid, 3-hydroxy-7-methyl-6-octenoic acid, malic acid, 3-hydroxysuccinic acid-methylester, 3-hydroxyadipinic acid-methylester, 3-hydroxysuberic acid-methylester, 3-hydroxysebacic acid-methylester, 3-hydroxyazelaic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-heptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid and 3-hydroxy-2,6-dimethyl-5-heptenoic acid.

In yet another aspect, the present invention provides 3HA having three to twelve carbons and lactate copolymer[poly(3HA-co-lactate)].

Other features and embodiments of the present invention will be more fully apparent from the following detailed description and appended claims.

DESCRIPTION OF THE PREFERRED EMBODIMENTS

Figure 1:
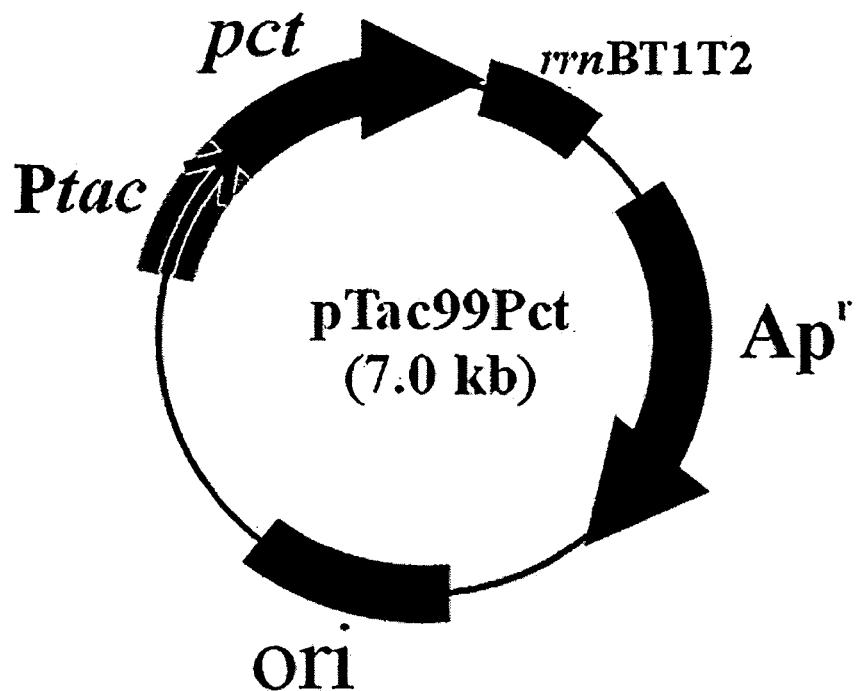
FIG. 1 is a gene map of recombinant plasmid pTac99Pct containing pct derived from *Clostridium propionicum*.

The present invention, in one aspect, relates to cells or plants having the ability of producing polylactate or hydroalkanoate-lactate copolymers[poly(hydroxyalkanoate-co-lactate)], which simultaneously have a gene encoding an enzyme converting lactate into lactyl-CoA and a gene encoding hydroxyalkanoates (PHA) synthase capable of using lactyl-CoA as a substrate.

The cells or plants having the ability of producing polylactate or hydroxyalkanoate-lactate copolymers[poly(hydroxyalkanoate-co-lactate)] are obtained by:

(i) transforming cells or plants lacking a gene encoding PHA synthase with a gene encoding an enzyme that converts lactate into lactyl-CoA and a gene encoding PHA synthase that can use lactyl-CoA as a substrate, or (ii) transforming cells or plants having a gene encoding PHA synthase for which lactyl-CoA is a substrate with a gene encoding an enzyme that converts lactate into lactyl-CoA, or (iii) transforming cells or plants having a gene encoding an enzyme that converts lactate into lactyl-CoA with a gene encoding PHA synthase for which lactyl-CoA is a substrate However, the invention is not limited to the foregoing. For example, the invention includes a cell having one or both of (1) a gene encoding PHA synthase for which lactyl-CoA is a substrate and (2) a gene encoding an enzyme converting lactate into lactyl-CoA. One of these genes may be amplified and the other gene transformed into the cell.

In the present invention, a gene encoding an enzyme that converts lactate into lactyl-CoA is preferably propionyl-CoA transferase (pct). The cells or plants are preferably transformed with a recombinant vector comprising the pct gene, and also transformed with a vector comprising phaRBC or phaRBC, preferably inserted onto the cells' or plants' chromosome(s). In this case, if lactate or hydroxyalkanoate and lactate are used as a carbon sources, it is possible to make polylactate or hydroxyalkanoate-lactate copolymers [poly (hydroxyalkanoate-co-lactate)]. Furthermore, a preferred gene encoding PHA synthase for which lactyl-CoA is a substrate is phaC. The cells or plants are preferably transformed with a recombinant vector comprising the pct gene, also transformed with a vector comprising phaC or phaC which is preferably inserted into a chromosome. In this case, if a fatty acid and lactate are used as a carbon source, it is possible to make a copolymer[poly(3HA-co-lactate)] of 3HA that has three to twelve carbons and lactate.

As is known in the art, various microorganisms have a gene encoding PHA synthase (KR 10-250830 B1). The following are examples of such microorganisms: microorganisms of the genus *Achromobacter* that include *Achromobacter* sp., *Achromobacter xylosoxidans*, etc., microorganisms of the genus *Acinetobacter* that include *Acidovorax delafieldii*, *Acidovorax facilis*, *Acinetobacter* sp., *Acinetobacter calcoaceticus*, *Acinetobacter lwoffii*, etc., microorganisms of the genus *Aeromonas* that include *Actinomyces* sp., *Aeromonas caviae*, *Aeromonas hydrophila*, *Aeromonas salmonicida*, etc., microorganisms of the genus *Alcaligenes* that include *Alcaligenes aestus*, *Alcaligenes denitrificans*, *Alcaligenes eutrophus*(after renamed as *Ralstonia eutropha*, it is renamed as *Wauteisia eutropha*); *Alcaligenes faecalis*; *Alcaligenes latus*, *Alcaligenes pacificus*, *Alcaligenes paradoxus*, *Alcaligenes venestus*, etc. microorganisms of the genus *Amoebobacter* that include *Alteromonas macleodii*, *Amoebobacter roseu*, *Amoebobacter pendens*, etc., microorganisms of the genus *Azospirillum* that include *Aphanocapa* sp., *Aphanothece* sp., *Aquaspirillum autotrophicum*, *Azorhizobium caulinodans*, *Azospirillum* sp., *Azospirillum brasilense*, *Azospirillum lipoferum*, etc., microorganisms of the genus *Azotobacter* that include *Azotobacter* sp., *Azotobacter agilis*, *Azotobacter chroococcum*, *Azotobacter macrocytogenes*, *Azotobacter vinelandii*, etc., microorganisms of the genus *Bacillus* that include *Bacillus anthracis*, *Bacillus cereus*, *Bacillus megaterium*, *Bacillus subtillus*, *Bacillus thuringiensis*, etc., microorganisms of the genus *Beggiatoa* that include *Beggiatoa* sp., *Beggiatoa alba*, etc., microorganisms of the genus *Beijerinckia* that include *Beijerinckia indicus*, *Beijerinckia mobilis*, etc., microorganisms of the genus *Beneckea* that include *Beneckea natrigens*, *Beneckea pelagia*, etc., microorganisms of the genus *Caulobacter* that include *Bordetella pertussis*, *Bradyrhizobium japonicum*, *Caryophamon latum*, *Caulobacter bacteroides*, *Caulobacter crescentus*, etc., microorganisms of the genus *Chlorogloea* that include *Chloroflexus aurantiacus*, *Chlorogloea fritschii*, etc., microorganisms of the genus *Chromatium* that include *Chromatium minutissimum*, *Chromatium okenii*, *Chromatium tepidum*, etc., microorganisms of the genus *Chromobacterium* that include *Chromobacterium violaceum*, etc., microorganisms of the genus *Clostridium* that include *Clostridium botulinum*, *Clostridium sphenoides*, etc., microorganisms of the genus *Comamonas* that include *Comamonas acidovorans*, *Comamonas testosteroni*, etc., microorganisms of the genus *Corynebacterium* that include *Corynebacterium autotrophicum*, *Corynebacterium hydrocarboxydans*, etc., microorganisms of the genus *Derxia* that include Cyanobacteria, *Derxia gummosa*, etc., microorganisms of the genus *Desulfonema* that include *Desulfococcus multivorans*, *Desulfonema limicola*, *Desulfonema magnum*, etc., microorganisms of the genus *Ectothiorhodospira* that include *Desulfosacina variabilis*, *Desulfovibrio sapovorans*, *Ectothiorhodospira halochloris*, *Ectothiorhodospira mobilis*, *Ectothiorhodospira vacuolata*, etc., microorganisms of the genus *Halobacterium* that include *Ferrobacillus ferroxidans*, *Flavobacterium* sp., *Haemophilus influenzae*, *Halobacterium gibbonsii*, *Halobacterium volcanii*, etc., microorganisms of the genus *Hydrogenophaga* that include *Haloferax mediterranei*, *Hydroclathratus clathratus*, *Hydrogenomonas facilis*, *Hydrogenophaga flava*, *Hydrogenophaga pseudoflava*, *Hydrogenophaga taeniospiralis*, etc., microorganisms of the genus *Hyphomicrobium* that include *Hyphomicrobium vulgare*, etc., microorganisms of the genus *Methylobacterium* that include *Ilyobater delafieldii*, *Labrys monachus*, *Lamprocystis reseopersicina*, *Lampropedia hyaline*, *Legionella* sp., *Leptothrix discophorus*, *Methylobacterium* AM1, *Methylobacterium extorquens*, etc., microorganisms of the genus *Methylosinus* that include *Methylococcus thermophilus*, *Methlocystis parvus*, *Methylomonas methanica*, *Methylosinus sporium*, *Methylosinus trichosporium*, etc., microorganisms of the genus *Micrococcus*, that include *Methylovibrio soehngenii*, *Micrococcus denitrificans*, *Micrococcus halodenitrificans*, etc., microorganisms of the genus *Mycobacterium* that include *Mycobacterium album*, *Mycobacterium vacae*, etc., microorganisms of the genus *Nitrobacter* that include *Nitrobacter agilis*, *Nitrobacter winogradskyi*; etc., microorganisms of the genus *Nocardia* that include *Nocardia alba*, *Nocardia asteroides*, *Nocardia lucida*, *Nocardia rubra*, etc., microorganisms of the genus *Photobacterium* that include *Paracoccus dentrificans*, *Oscillatoria limosa*, *Penicillium cyclopium*, *Photobacterium mandapamensis*, *Photobacterium phosphoreum*, etc., microorganisms of the genus *Pseudomonas* that include *Physarum ploycephalum* and *Pseudomonas glathei*, *Pseudomonas indigofera*, *Pseudomonas lemonieri*, *Pseudomonas mallei*, *Pseudomonas marina*, *Pseudomonas mixta*, *Pseudomonas oleovorans*, *Pseudomonas oxalaticus*, *Pseudomonas pseudoalcaligenes*, *Pseudomonas aeruginosa*, *Pseudomonas alcaligenes*, *Pseudomonas asplenii*, *Pseudomonas butanovora*, *Pseudomonas cepacia*, *Pseudomonas coronafaciens*, *Pseudomonas dacunhae*, *Pseudomonas denitrificans*, *Pseudomonas diminuta*, *Pseudomonas echinoides*, *Pseudomonas fluorescens*, *Pseudomonas putida*, *Pseudomonas rubrilineas*, *Pseudomonas saccharophila*, *Pseudomonas stutzeri*, *Pseudomonas syringae*, *Pseudomonas thermophilus*, *Pseudomonas viridiflava*, etc., microorganisms of the genus *Ralstonia*, microorganisms of the genus *Rhizobium* that include *Rhizobium hedysarum*, *Rhizobium lupini*, *Rhizobium meliloti*, *Rhizobium phaseoli*, *Rhizobium trifoli*, etc., microorganisms of the genus *Rhodobacillus*, microorganisms of the genus *Rhodobacter* that include *Rhodobacter capsulatus*, *Rhodobacter sphaeroides*, etc., microorganisms of the genus *Rhodococcus* that include *Rhodococcus rhodochrous*, etc., microorganisms of the genus *Rhodocyclus* that include *Rhodocyclus gelatinosus*; *Rhodocyclus tenuis*, etc., microorganisms of the genus *Rhodopseudomonas* that include *Rhodomicrobium vannielii* and *Rhodopseudomonas acidophila*, *Rhodopseudomonas capsulata*, etc., microorganisms of the genus *Rhodospirillum* that include *Rhodospirillum molischianum*, *Rhodospirillum rubrum*, etc., microorganisms of the genus *Spirillum* that include *Sphingomonas paucimobilis*, *Spirillum itersomii*, *Spirillum serpens*, etc., microorganisms of the genus *Spirulina* that include *Spirulina jenneri*, *Spirulina maxima*, *Spirulina subsaksa*, etc., microorganisms of the genus *Staphylococcus* that include *Staphylococcus aureus*, *Staphylococcus epidermidis*, *Staphylococcus xylosus*, etc., microorganisms of the genus *Stella* that include *Stella humosa*, *Stella vacuolata*, etc., microorganisms of the genus *Streptomyces* that include *Streptomyces antibioticus*, *Streptomyces coelicolor*, etc., microorganisms of the genus *Thiobacillus* that include *Syntrophomonas wolfei*, *Thermophilic cyanobacteria*, *Thermus thermophilus*, *Thiobacillus* A2, *Thiobacillus acidophilus*, *Thiobacillus versutus*, etc., microorganisms of the genus *Thiocapsa* that include *Thiocapsa pfennigii*, etc., microorganisms of the genus *Zoogloea* that include *Thiocystis violacea*, *Vibrio parahaemolyticus*, *Xanthobacter autotrophicus*, *Xanthomonas maltophilia*, *Zoogloea ramigera*, etc.

The present invention also provides to a method for preparing polylactate or hydroxyalkanoate-lactate copolymer [poly(hydroxyalkanoate-co-lactate)], comprising culturing (a) culturing cells in a medium containing lactate or lactate and hydroxyalkanoate as a carbon source and recovering polylactate or hydroxyalkanoate-lactate copolymer from the cultured cells or (b) culturing the plants; and recovering polylactate or hydroxyalkanoate-lactate copolymer from the cultured plants.

In the present invention, hydroxyalkanoate-lactate copolymer[poly(hydroxyalkanoate-co-lactate)] is preferably poly (3HB-co-lactate), poly(4HB-co-lactate), poly(3HP-co-lactate), poly(3HB-co-4HB-co-lactate) or poly(3HP-co-4HB-co-lactate), but it is not limited to these copolymers. For example, in hydroxyalkanoate-lactate copolymer [poly(hydroxyalkanoate-co-lactate)] according to the present invention, the hydroxyalkanoate may be one or more of 3-hydroxybutyrate, 3-hydroxyvalerate, 4-hydroxybutyrate, (D)-3-hydroxycarboxylic acids of the medium chain length(C6-14), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxysuberic acid-methylester, 3-hydroxyazelaic acid-methylester, 3-hydroxysebacic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethyl-5-heptenoic acid.

The present invention is also directed to a recombinant vector for preparing polylactate or hydroxyalkanoate-lactate copolymer[poly(hydroxyalkanoate-co-lactate)] which comprises a gene encoding an enzyme that converts lactate to lactyl-CoA and a gene encoding PHA synthase that uses lactyl-CoA as a substrate, and cells or plants transformed with this recombinant vector.

The term "vector" means a DNA construct comprising DNA sequence operably linked to a suitable control sequence capable of expressing the DNA in a suitable host. In the present invention, plasmid vector, bacteriophage vector, cosmid vector, YAC (Yeast Artificial Chromosome) vector can be used as the above vector and it is preferable to use plasmid vector for the purpose of the present invention. Typical plasmid vectors that can be used for these purposes have (a) an origin of replication so that it leads to effective replication so that each host cell contains several hundred copies of plasmid vector (b) an antibiotic-resistance gene so that a host cell transformed with a plasmid vector can be selected and (c) a sequence comprising a restriction enzyme site where a foreign DNA fragment is to be inserted. Even in the absence of a suitable restriction enzyme site, a vector or foreign DNA can easily be ligated by using a synthetic oligonucleotide adaptor or a linker according to conventional methods.

After ligation, a vector is transformed into a suitable host cell. Prokaryotic cells or eukaryotic cells can be used, more preferably, prokaryotic cells. Microorganisms lacking PHA synthase, such as *E. coli*, as well as microorganisms having PHA synthase, can be used as a suitable prokaryotic host cell. Also, *E. coli* transformed with a gene encoding PHA synthase can be used as the cell/microorganism that comprises the PHA synthase-encoding gene. Preferable strains of *E. coli* include: *E. coli* DH5a, *E. coli* JM101, *E. coli* K12, *E. coli* W3110, *E. coli* X1776, *E. coli* XL1-Blue(Stratagene) and *E. coli* B. However, *E. coli* strains such as FMB101, NM522, NM538 and NM539 and other prokaryotic species and genera can also be used. In addition to *E. coli* and microorganisms having a gene encoding PHA synthase, the genus *Agrobacterium*, such as *Agrobacterium* A4, the genus *Bacilli*, such as *Bacillus subtilis*, and various enterobacteria such as *Salmonella typhimurium* or *Serratia marcescens* can be used herein as host cells. The "universal" eukaryotic host cells, such as yeast, fungi, insect cells (for example, from *Spodoptera frugiperda* (SF9)), animal cells, such as CHO, mouse cells, cultured human cell lines and plant cells can also be used. In a suitable host transformed with a vector, the vector can replicate and function regardless of a host genome, or can, in some cases, be incorporated into the genome.

As is generally known in the art, for high expression level of a transformed gene in a host cell, the gene must be operably linked to transcription, translation and expression regulating sequences functioning in a selected expression host. The expression control sequence and the corresponding gene are preferably positioned in one expression vector that comprises both a selectable marker of bacterial origin and an origin or replication. For expression in a eukaryotic host cell, the expression vector should additionally comprise an expression marker useful in the eukaryotic host.

A cell transformed by aforementioned expression vector cell is also included in the present invention. The term "transformation" as used herein means that DNA can replicate extrachromosomally or as part of the entire chromosome following introduction of the DNA into a host cell.

It is to be understood that not all vectors and expression regulatory sequences function equally in expressing a DNA sequence of the present invention. Also, not all hosts function equally with the same expression system. However, a person skilled in the art can readily select from among several vectors, expression control sequences and hosts without undue experimentation as is intended in the scope of the present invention. For example, when selecting a vector, the host cell to be transformed must be considered because the vector must replicate in the host. The replication number of a vector, the ability of controlling replication number and the expression of other proteins encoded by the corresponding vector (for example, an antibiotic marker) should also be considered. With conventional knowledge of these variables, a person skilled in the art will know how to select various combinations of vector, expression regulatory sequence and host which are suitable for the present invention.

Transformation of plants can be achieved by conventional methods using *Agrobacterium* or virus vectors. For example, transformed plants are obtained by transforming an *Agrobacterium* with a recombinant vector containing the inventive gene and infecting a tissue, etc. of the target plant with the transformed *Agrobacterium*. For example, transformed plants suitable for the present invention can be obtained by a method that is the same or similar to those disclosed in PCT Publication WO 94/11519 and U.S. Pat. No. 6,103,956) which disclose PHA preparation using transformed plants.

Transformed plants useful for the present invention include, but are not limited to, tobacco, tomato, red peppers, beans, nice, and corn. Also, even though a transformed plants is one that propagates sexually, it will be obvious to a person skilled in the art that such a plant can be reproduced asexually using plant tissue culture, etc.

The present invention also relates to a method for preparing polylactate or hydroalkanoate-lactate copolymer[poly(hydroalkanoate-co-lactate)] comprising (a) culturing the transformed cells in a medium containing lactate or hydroalkanoate and lactate as a carbon source; and recovering polylactate or hydroxyalkanoate-lactate copolymer from the cultured cell or (b) culturing the transformed plants and recovering polylactate or hydroxyalkanoate-lactate copolymer from the cultured plants.

The present invention further relates to hydroalkanoate-lactate copolymer [poly(hydroalkanoate-co-lactate)] that comprises, as a monomer, lactate and one or more hydroalkanoates selected from 3-hydroxybutyrate, 3-hydroxyvalerate, 4-hydroxybutyrate, (D)-3-hydroxycarboxylic acids of the medium chain length(C6-14), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxysuberic acid-methylester, 3-hydroxyazelaic acid-methylester, 3-hydroxysebacic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid or 3-hydroxy-2,6-dimethyl-5-heptenoic acid.

In the present invention, the hydroalkanoate preferably comprises 3HB and 4HB or 3HP and 4HB.

The present invention, in yet another aspect, provides a copolymer [poly(3HA-co-lactate)] of 3HA having three to twelve carbons and lactate.

In the present invention, the copolymer of 3HA having three to twelve carbons and lactate is preferably [poly(3HHx-co-3HO-co-3HD-co-lactate)] or [poly(3HHx-co-3HO-co-3HD-co-3HDD-lactate)].

Figure 2:
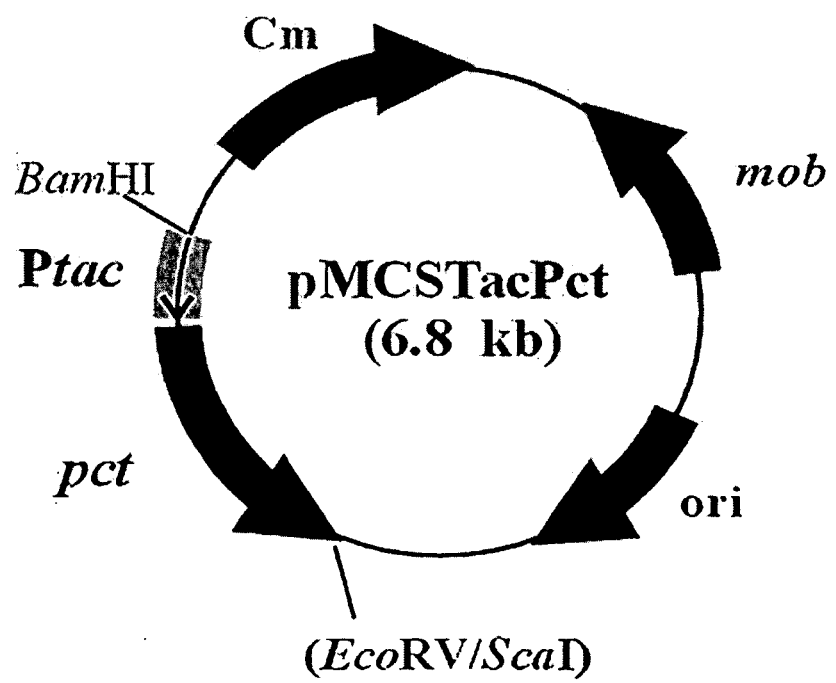
FIG. 2 is a gene map of recombinant plasmid pMCSTac99Pct containing pct derived from *Clostridium propionicum*.
Figure 3:
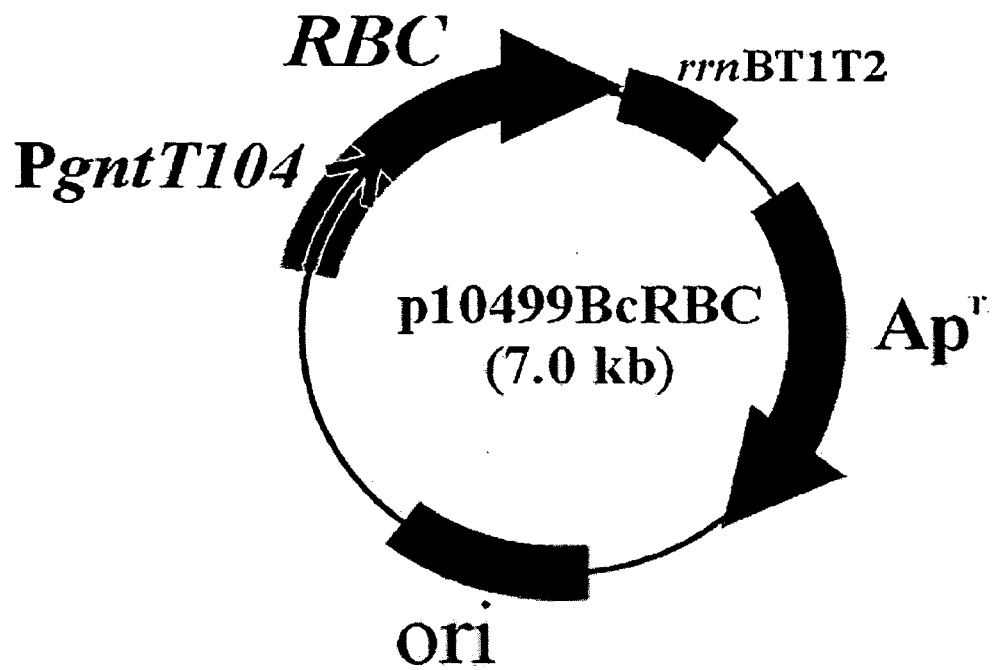
FIG. 3 is a gene map of recombinant plasmid p10499BcRBC containing phaRBC derived from *Bacillus cereus*.
Figure 4:
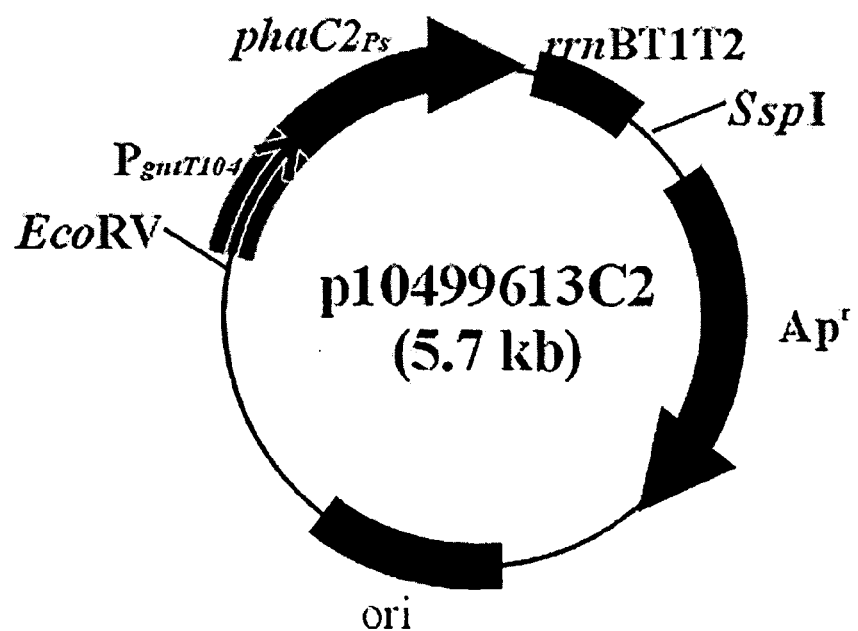
FIG. 4 is a gene map of recombinant plasmid p10499613C2 containing phaC2$_{PS}$, a gene encoding PHA synthase derived from *Pseudomonas* sp. 61-3.

After a gene encoding an enzyme which converts lactate into lactyl-CoA (Pct) was inserted into pTac99A to construct an expression vector designated pTac99Pct (FIG. 1), the gene fragment containing tac promoter, the pct gene, transcription terminator from the vector pTac99Pct was inserted into pBBRIMCS to construct a recombinant expression vector pMCSTacPct (FIG. 2). Also, a gene encoding PHA synthase derived from *Bacillus cereus* ATCC 14579(phaRBC) was inserted into the p10499A vector to construct a recombinant expression vector p10499BcRBC (FIG. 3). A gene encoding PHA synthase derived from *Pseudomonas* SP. 61-3(phaC) was amplified and inserted into p10499A to construct recombinant expression vector p10499613C2 (FIG. 4).

It is well known that various PHA's and their copolymers can be prepared according to the kinds of carbon sources used (KR 10-250830 B1; Lee, *Biotechnol. Bioeng.*, 49:1, 1996; Steinbuchel and Valentin, *FEMS Microbiol. Lett.*, 128:219, 1995). All hydroxyalkanoates including (3-hydroxypropionate(3HP), 4-hydroxybutyrate(4HB), 3-hydroxybutyrate (3HB), 3-hydroxyhexanoate (3HHx), 3-hydroxyoctanoate (3HO), 3-hydroxydecanoate (3HD), 3-hydroxydodecanoate (3HDD), etc.) can comprise as a PHA monomer. It is possible to prepare PHA comprising various monomers and molecular composition ratios. That is, depending upon the carbon source used in culture, one can prepare a hydroxyalkanoate-lactate-copolymer which contains a hydroxyalkanoate, such as 3-hydroxybutyrate, 3-hydroxyvalerate, 4-hydroxybutyrate, (D)-3-hydroxycarboxylic acids of the medium chain length(C6-14), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxy-hexanoic acid, 4-hydroxy-heptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methyl-heptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyl-decanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxy-suberic acid-methylester, 3-hydroxyazelaic acid-methylester, 3-hydroxysebacic acid-methyl-ester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-penylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid and 3-hydroxy-2,6-dimethyl-5-heptenoic acid. In addition to the above saturated compounds, copolymers which comprise hydroxyalkanoates having double or triple bonds as monomers can be prepared. Therefore, "hydroxyalkanoate" as used herein is defined as including hydroxyalkanoates with double or triple bonds.

Therefore, using cells or plants transformed with the recombinant vectors of the present invention, it is possible to prepare copolymers [poly(hydroxyalkanoate-co-lactate)] of lactate and various hydroxyalkanoates as well as PLA (FIG. 5-FIG. 8).

Figure 5:
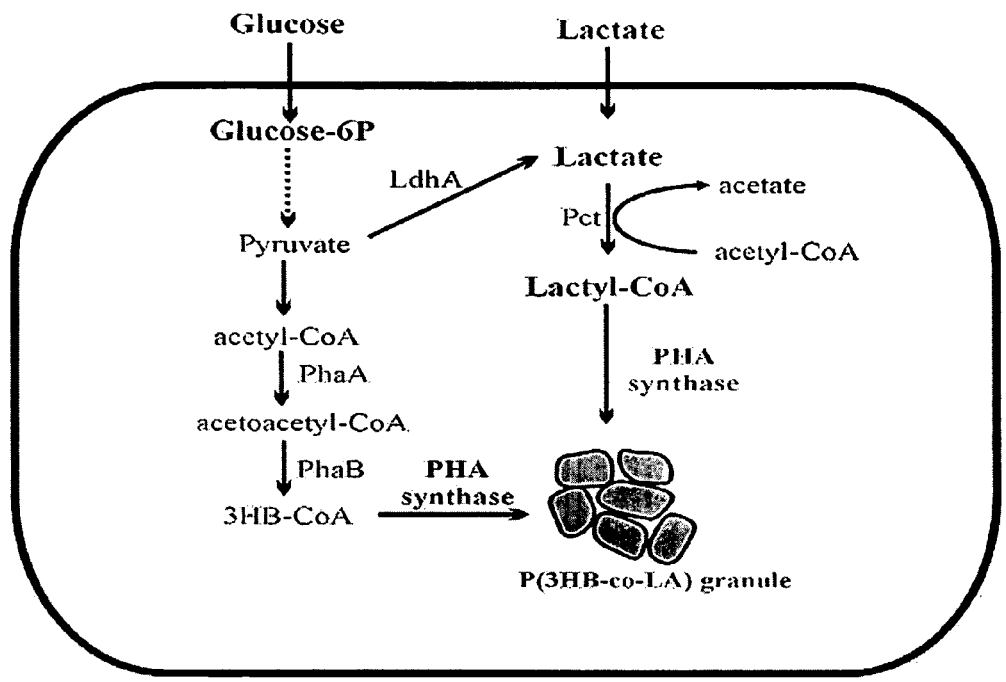
FIG. 5 is a schematic diagram showing a pathway for synthesizing P(3HB-co-lactate) using glucose and lactate.
Figure 6:
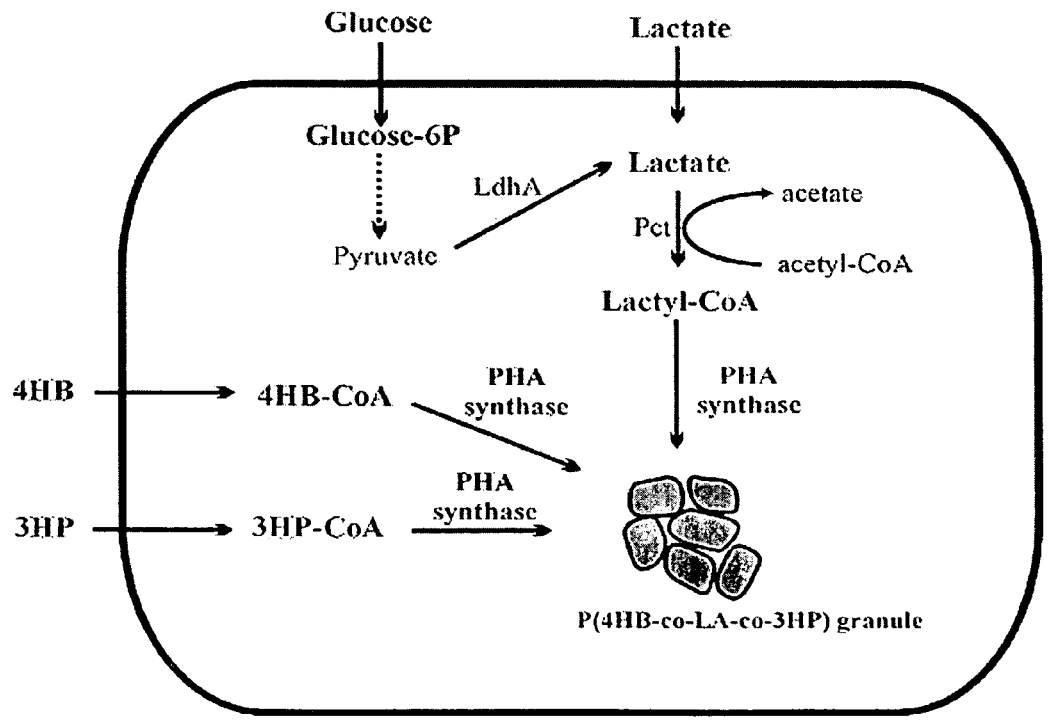
FIG. 6 is a schematic diagram showing a pathway for synthesizing copolymer P(3HB-co-4HB-co-lactate) using glucose, 4HB, 3HP and lactate.

In the case where *Ralstonia eutropha* NCIMB11599 comprising a gene encoding PHA synthetase that uses lactyl-CoA as a substrate is transformed with a plasmid containing propionyl-CoA transferase (pct) to produce a recombinant *Ralstonia eutropha*; the recombinant By culturing *Ralstonia eutropha* in a medium containing lactate or lactate and various carbon sources, various combinations of copolymers can be prepared. For example, when this recombinant *Ralstonia eutropha* is cultured in a production medium containing lactate, poly(3HB-co-lactate) can be prepared (FIG. 5). Also, when the recombinant *Ralstonia eutropha* is cultured in a production medium containing 3HB, 4HB and lactate, poly(3HB-co-4HB-co-lactate) can be prepared (FIG. 6).

Figure 7:
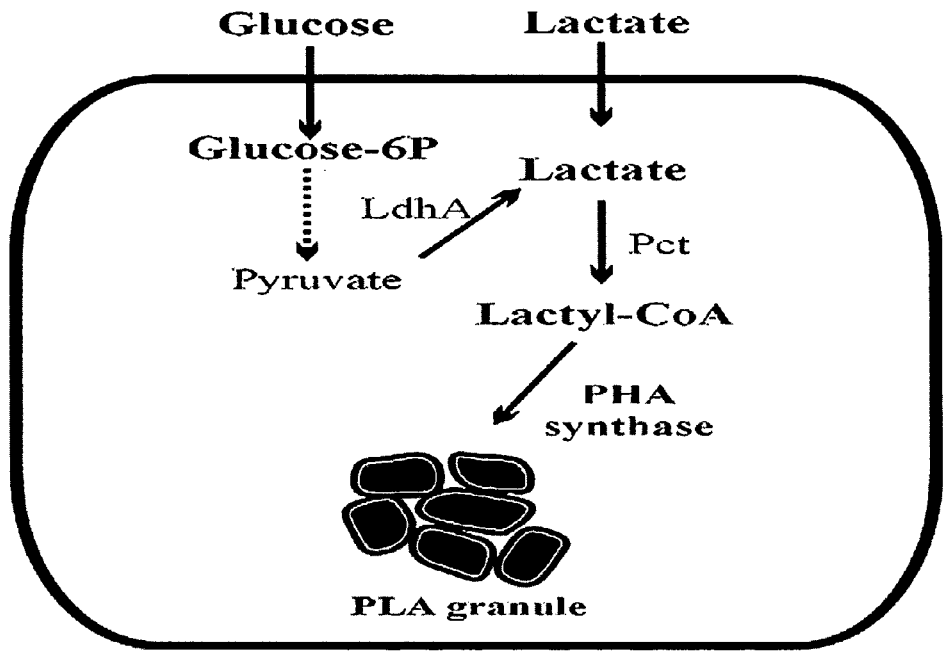
FIG. 7 is a schematic diagram showing a pathway for synthesizing PLA using cells.

Culturing recombinant *E. coli* transformed with a recombinant vector comprising phaRBC derived from *Bacillus cereus*(ATCC 14579) and a recombinant vector comprising pct (or a recombinant *E. coli* transformed with a recombinant vector that includes both phaRBC and pct) in a production medium supplemented with lactate, permits production of polylactate (FIG. 7). If such recombinant *E. coli* is cultured in medium supplemented with lactate and various carbon sources, several combinations of copolymers can be prepared.

Figure 8:
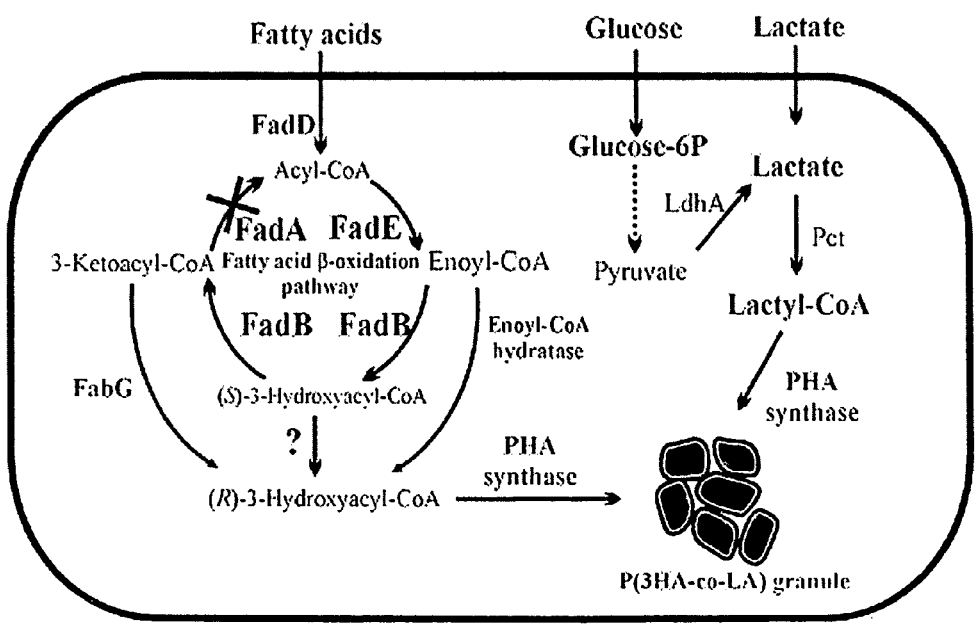
FIG. 8 is a schematic diagram showing a pathway for synthesizing copolymers P(3HA-co-lactate) containing medium chain length 3-hydroxyalkanoate(3HA) having three to twelve carbons and lactate as a monomer.

It was confirmed in KR 10-0447531B1 that culturing a recombinant *E. coli* WB101 transformed with p10499613C2 in a medium containing decenoic acid or a medium containing dodecenoic acid, respectively, results in production of a copolymer comprising 3HHx, 3HO and 3HD on the one hand and a copolymer containing 3HHx, 3HO, 3HD and 3HDD on the other. Therefore, culturing of recombinant *E. coli* transformed with a recombinant vector comprising a gene encoding PHA synthase (phaC) derived from *Pseudomonas* sp. 61-3 and a recombinant vector comprising pct (or *E. coli* transformed with a recombinant vector comprising both phaC and pct) in a production medium containing lactate and fatty acid, production of a copolymer [poly(3HA-co-lactate)] containing MCL-PHA monomers($C_{3-12}$) and lactate occurs (FIG. 8). For example, culturing of recombinant *E. coli* in medium containing (a) lactate or (b) decenoic acid, results in production of [poly(3HHx-co-3HO-co-3HD-co-lactate)]. Culturing of recombinant *E. coli* in medium containing (a) lactate or (b) dodecenoic acid results in production of [poly(3HHx-co-3HO-co-3HD-co-3HDD-lactate)].

The media used for biological production of polylactate and its copolymer is not limited to the extent that it does not interfere with the purposes of the present invention. In the present examples, a complex medium, Luria-Bertani(LB) medium was used for culture of recombinant *E. coli* and a basic medium, N-limited MR medium, was used for culture of recombinant *Ralstonia eutropha*.

Hereinafter, the present invention will be described in more detail by specific examples. However, the present invention is not limited to these examples, and it is obvious to those skilled in the field of the present invention that numerous variations or modifications could be made within the spirit and scope of the present invention.

EXAMPLES

Although pct was used as a gene encoding the enzyme that converts lactate into lactyl-CoA to serve as the substrate for PHA polymerase in the Examples below, it is obvious to those skilled in the art that a transferase derived from another microorganism will yield the same result.

Also, although the Examples below exemplify phaC derived from *Pseudomonas* sp. 61-3 and phaRBC derived from *Bacillus cereus*(ATCC 14579) as a gene encoding PHA synthase for which lactyl-CoA is a substrate, it is obvious to those skilled in the art that the same result will be obtained when PHA synthase having a similar substrate specificity is derived from various kinds of microorganisms, such as *Wautersia eutropha, Alcaligenes latus, Sinorhizobium meliloti, Bacillus megaterium, Chromatium vinosum*, etc.

Also, *E. coli* and *Ralstonia eutropha* are exemplified below as microorganisms respectively lacking, and having a gene encoding PHA synthase. However, it will be obvious to those skilled in the art that the same result can be obtained when other kinds of cells such as bacteria, yeast, fungi, animal cells and plant cells, as well as plants, are used.

Example 1

Construction of Recombinant Vector Containing pct

Primers having basic sequences of shown below were synthesized based on the pct gene sequence (Selmer et al., *Eur J. Biochem.*, 269:372, 2002) for PCR cloning of pct:

SEQ ID NO: 1:
5'-ggaattcATGAGAAAGGTTCCCATTATTACCGCAGATGA-3'

SEQ ID NO: 2:
5'-gctctagattaggacttcatttccttcagacccattaagccttctg-3'

To amplify pct, PCR was carried out using chromosomal DNA of *Clostridium propionicum* as template and the above primers. PCR was performed under conditions of 30 cycles (denaturation at 94° C., for 50 sec annealing at 52° C., for 50 sec extension at 72° C., for 2 min). By examining the PCR reaction product by agarose gel electrophoresis, a 1.5 Kb gene fragment corresponding to pct was observed. After the pTac99A vector (Park and Lee, *J. Bacteriol.*, 185:5391, 2003) was digested with EcoRI/XbaI enzyme, pTac99Pct recombinant expression vector was prepared by inserting pct into EcoRI/XbaI recognition site of pTac99A (FIG. 1). Also, pMCSTacPct was prepared by inserting a gene fragment obtained by digesting pTac99Pct with BamHI/ScaI into pBRR1MCS (Kovach et al., *Gene*, 166:175, 1995) digested with BamHI/EcoRV (FIG. 2).

Example 2

Construction of Recombinant Vector Containing a Gene Encoding PHA Synthase

To amplify phaRBC operon, PCR was carried out using chromosome DNA of *Bacillus cereus* as template and the following primers.

SEQ ID NO: 3:  5'-ggaattcatgaattgtttcaaaaacga-3'

SEQ ID NO: 4:  5-cgggatccttaattagaacgctcttcaa-3'

PCR was performed under the condition of 30 cycles (denaturation at 94° C., for 50 sec annealing at 52° C., for 50 sec extension at 72° C., for 2 min), Upon examination of the PCR reaction product by agarose gel electrophoresis, a 2.5 Kb gene fragment corresponding to phaRBC was observed. After p10499A vector(KR 10-0447531B1) was digested with EcoRI/BamHI enzyme, a p10499BcRBC recombinant expression vector was prepared by inserting phaRBC into the EcoRI/BamHI recognition site of p10499A (FIG. 3).

Also, a gene encoding PHA polymerase (phaC) derived from *Pseudomonas* sp. 61-3 was amplified and inserted into p10499A to prepare the recombinant expression vector p10499613C2(KR 10-0447531B1) (FIG. 4).

Example 3

Construction of Recombinant *Ralstonia eutropha* and Preparation of Hydroalkanoate-Lactate Copolymer Using the Same After recombinant *Ralstonia eutropha* (pMCSTacPct) was constructed by introducing pMCSTacPct prepared in Example 1 into *Ralstonia eutropha* NCIMB11599, two-step culture was carried out. After recombinant *Ralstonia eutropha* was cultured in a NB medium(Nutrient Broth; 5 g/L of Peptone, 3 g/L of Beef extract) overnight, the strains recovered by centrifugation were cultured in a N-limited MR medium containing 2 g/L of lactate for 3 days. The composition of N-limited MR medium was as follows: 6.67 g of $KH_2PO_4$, 4 g Of $(NH_4)_2HPO_4$, 0.8 g of $MgSO_4.7H_2O$, 0.8 g of citric acid, and 5 mL of trace metal solution. Trace metal solution(per liter): 5 mL of 5M HCl, 10 g of $FeSO_4.7H_2O$, 2 g of $CaCl_2$, 2.2 g of $ZnSO_4. 7H_2O$, 0.5 g of $MnSO_4.4H_2O$, 1 g of $CuSO_4.5H_2O$, 0.1 g of $(NH_4)_6Mo^7O_{24}.4H_2O$, and 0.02 g of $Na_2B_4O_2.10H_2O$.

Figure 9:
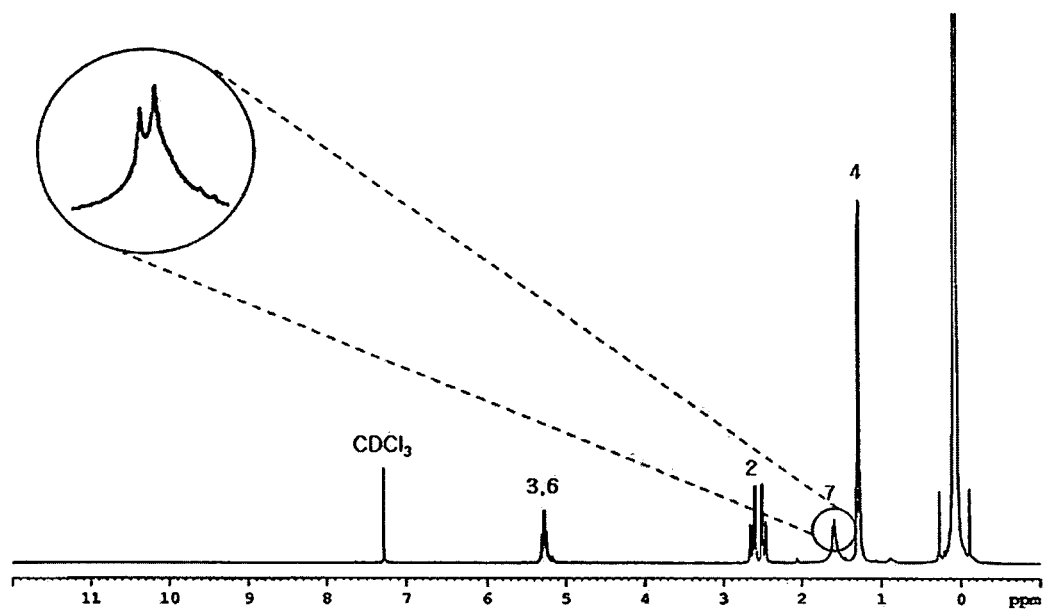
FIG. 9 is $^1$H-NMR result of P(3HB-co-LA) prepared from *R. eutropha* NCIMB11599(pMCSTacPct).
Figure 9:
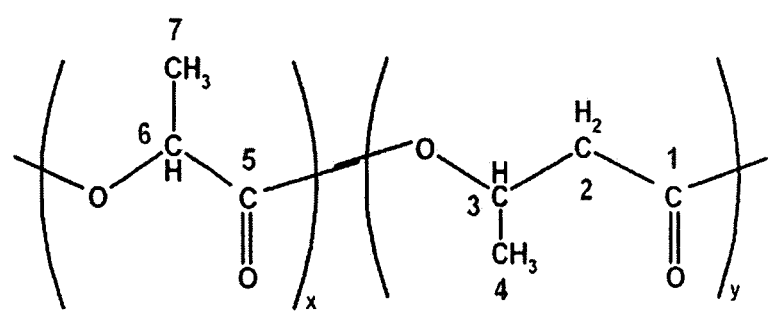
Figure 10:
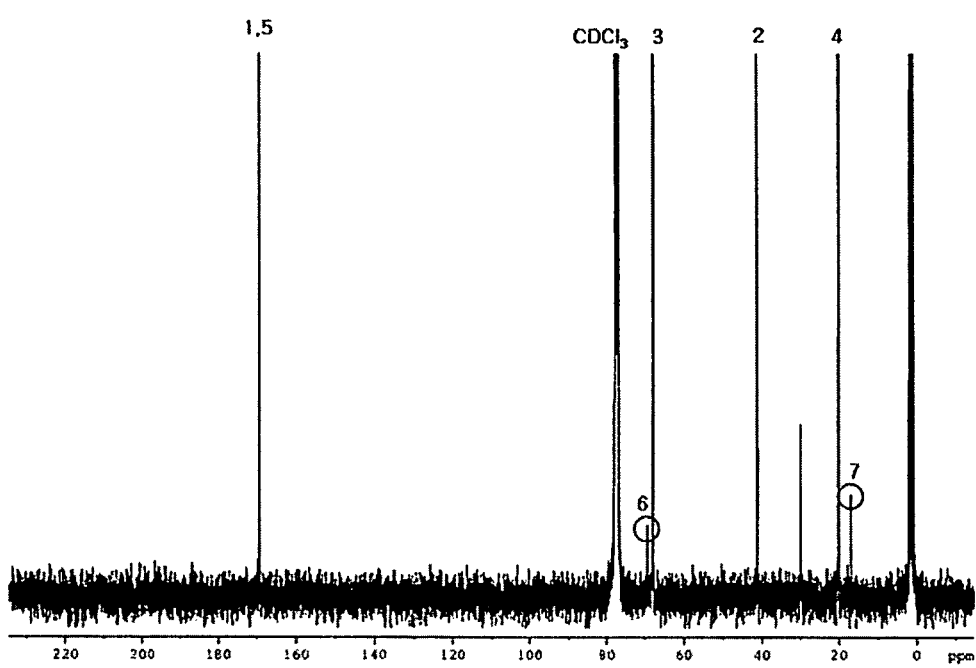
FIG. 10 is $^{13}$C-NMR result of P(3HB-co-LA) prepared from *R. eutropha* NCIMB11599(pMCSTacPct).

After the strains were recovered by centrifugation and freeze-dried, polymer substance accumulated in the strains was recovered using chloroform. As a result of NMR analysis on recovered polymer, it was confirmed that the above recovered polymer substance was poly(3HB-co-lactate) copolymer as shown in FIG. 9, FIG. 10.

Example 4

Figure 11:
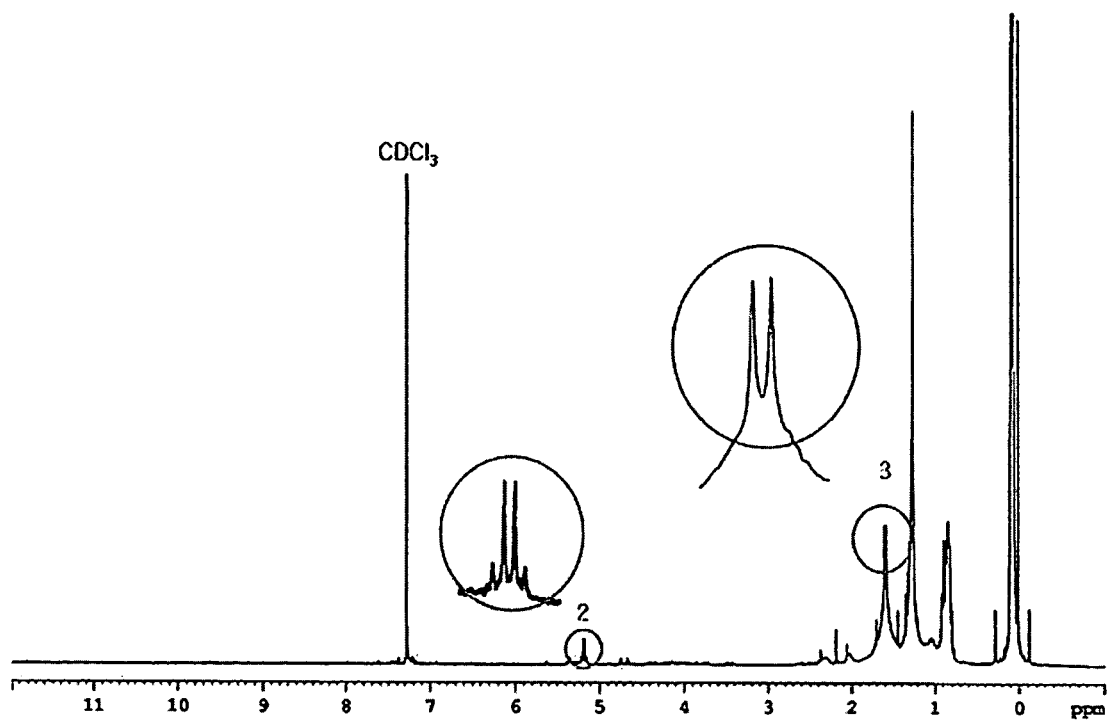
FIG. 11 is $^1$H-NMR result of PLA prepared from *E. coli* XL1-Blue(p10499BcRBC+pMCSTacPct).

Construction of Recombinant *E. coli* and Preparation of Copolymer of Polylactate and Hydroxyalkanoate-Lactate Using the Same Recombinant *E. coli* was constructed by introducing pMCSTacPct prepared in Example 1 and p10499BcRBC prepared in Example 2 into *E. coli* XL1-Blue and cultured in an LB medium containing 2 g/L of lactate for 4 days, followed by centrifuging to recover the strains. The recovered strains were freeze-dried to recover polymer substance accumulated in the strains using chloroform. As a result of NMR analysis on the recovered polymer, it was confirmed that the above obtained polymer substance was polylactate (FIG. 11).

Also, a recombinant *E. coli* was constructed by introducing pMCSTacPct prepared in Example 1 and p10499613C2 produced in Example 2 into *E. coli* WB101 [W3110(fadB::Km).

WB101 is a strain that is identified to be effective in producing MCL-PHA as fadB mutant E. coli(KR 10-044753B1). The recombinant E. coli WB101 was cultured in LB media containing 2 g/L of lactate and 2 g/L of decenoic acid for 4 days, respectively and centrifuged to recover strains. The recovered strains were freeze-dried to recover polymer substance accumulated in the strains using chloroform. As a result of NMR analysis on the obtained polymer substance, it was confirmed that the above recovered polymer was [poly (3HHx-co-3HO-co-3HD-co-lactate)] copolymer.

Although the present invention has been described in detail with reference to the specific features, it will be apparent to those skilled in the art that this description is only for a preferred embodiment and dose not limit the scope of the present invention. Thus, the substantial scope of the present invention will be defined by the appended claims and equivalents thereof.

UTILITY AND INDUSTRIAL APPLICABILITY

As described above in detail, the present invention provides cells or plants which express a gene encoding an enzyme that converts lactate into lactyl-CoA and a gene encoding PHA synthase that uses lactyl-CoA as a substrate, and a method for preparing polylactate or hydroxyalkanoate-lactate copolymer using these cells or plants. Polylactate can be prepared by using cells or plants and various kinds of polyesters containing lactate, and various hydroxyalkanoate monomers can be also prepared.

What is claimed is:

1. A method for preparing polylactate or hydroxyalkanoate-lactate copolymer [poly(hydroxyalkanoate-co-lactate)], comprising:

culturing a recombinant *E. coli* or *Ralstonia eutropha* in a medium containing lactate, or lactate and hydroxyalkanoates as a carbon source, wherein the recombinant *E. coli* or *Ralstonia eutropha* comprises a propionyl-CoA tranferase gene (pct) derived from *Clostridium propionicum*, and a gene selected from phaC derived from *Pseudomonas* sp. 61-3 and phaRBC derived from *Bacillus cereus*; and recovering polylactate or hydroxyalkanoate-lactate copolymer from the cultured *E. coli* or *Ralstonia eutropha*.

2. The method according to claim 1, wherein said hydroxyalkanoate-lactate copolymer is one or more hydroxyalkanoates selected from the group consisting of 3-hydroxybutyrate, 3-hydroxyvalerate, 4-hydroxybutyrate, a $C_{6-14}$ (D)-3-hydroxycarboxylic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxy-hexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyl-decanoic acid, 3-hydroxy-7-methyl-6-octenoic acid, malic acid, 3-hydroxysuccinic acid-methyl-ester, 3-hydroxyadipinic acid-methylester, 3-hydroxysuberic acid-methylester, 3-hydroxyazelaic acid-methylester, 3-hydroxysebacic acid-methylester, 3-hydroxyazelaic acid-methyl-ester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecenoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid and 3-hydroxy-2,6-dimethyl-5-heptenoic acid.

3. The method according to claim 2, wherein said hydroxyalkanoate-lactate copolymer is selected from the group consisting of poly(3HB-co-lactate), poly(4HB-co-lactate), poly(3HP-co-lactate), poly(3HB-co-4HB-co-lactate) and poly(3HP-co-4HB-co-lactate).

4. A method for preparing a copolymer of 3HA having three to twelve carbons and lactate [poly(3HA-co-lactate)], the method comprising:

culturing a recombinant *E. coli* or *Ralstonia eutropha* in a medium containing lactate and a fatty acid as a carbon source, wherein the recombinant *E. coli* or *Ralstonia eutropha* comprises a propionyl-CoA transferase gene (pct) derived from *Clostridium propionicum* and a gene selected from phaC derived from *Pseudomonas* sp. 61-3 and phaRBC derived from *Bacillus cereus*; and recovering said [poly(3HA-co-lactate)] from the cultured *E. coli* or *Ralstonia eutropha*.

5. The method according to claim 4, wherein the copolymer is [poly(3HHx-co-3HO-co-3HD-co-lactate)], and said fatty acid is decenoic acid and said 3HA is 3HHx, 3HO and 3HD.

6. The method according to claim 4, wherein the copolymer is [poly(3HHx-co-3HO-co-3HD-co-3HDD-lactate)], and said fatty acid is dodecenoic acid and said 3HA is 3HHx, 3HO, 3HD and 3HDD.

* * * * *